United States Patent
Huehne et al.

(10) Patent No.: US 10,054,526 B2
(45) Date of Patent: Aug. 21, 2018

(54) DEVICE FOR DETERMINING THE LOAD-BEARING CAPACITY OF A CYLINDRICAL SHELL INCLUDING AN AXIAL WORKING FORCE TO THE CYLINDRICAL SHELL AND DETECTING FAILURE OF THE CYLINDRICAL SHELL

(71) Applicant: Deutsches Zentrum fuer Luft- und Raumfahrt e.V., Cologne (DE)

(72) Inventors: Christian Huehne, Hannover (DE); Ronald Wagner, Magdeburg (DE); Steffen Niemann, Wolfsburg (DE)

(73) Assignee: Deutsches Zentrum fuer Luft- und Raumfahrt e.V., Cologne (DE)

( * ) Notice: Subject to any disclaimer, the term of this patent is extended or adjusted under 35 U.S.C. 154(b) by 0 days.

(21) Appl. No.: 15/378,115

(22) Filed: Dec. 14, 2016

(65) Prior Publication Data

US 2017/0276581 A1   Sep. 28, 2017

(30) Foreign Application Priority Data

Mar. 24, 2016  (DE) .................... 20 2016 101 634 U

(51) Int. Cl.
*G01N 3/20* (2006.01)
*G01N 3/30* (2006.01)
*G01N 3/08* (2006.01)

(52) U.S. Cl.
CPC .............. *G01N 3/08* (2013.01); *G01N 3/20* (2013.01); *G01N 2203/0085* (2013.01)

(58) Field of Classification Search
CPC ............ G01N 3/02; G01N 2203/0019; G01N 2203/0435; G01N 2203/0278; G01N 3/08;

(Continued)

(56) References Cited

U.S. PATENT DOCUMENTS

2005/0016264 A1* 1/2005 Anthe .................... G01N 3/307
                                                      73/82
2006/0191327 A1* 8/2006 Yang ........................ G01N 3/46
                                                      73/81

(Continued)

FOREIGN PATENT DOCUMENTS

DE          10344544 B3      1/2005

OTHER PUBLICATIONS

Wagner et al., Constant single-buckle imperfection principle to determine a lower bound for the buckling load of unstiffened composite cylinders under axial compression, Composite Structures, Dec. 15, 2015, vol. 139, pp. 120-129.

*Primary Examiner* — Harshad R Patel
*Assistant Examiner* — Brandi Hopkins
(74) *Attorney, Agent, or Firm* — W&C IP

(57) ABSTRACT

The load-bearing capacity of cylindrical shells of a composite fiber material that are at risk of buckling is determined by deriving improved reduction factors for analytical calculation of the design load. A load distribution head applies an axially acting force to a cylinder shell. A dent actuator dents the surface of the cylinder shell in a predetermined dent direction with a predetermined dent depth. A dent force is determined when a steadily increasing, axially acting force is applied to the cylinder shell by the load distribution head until a complete failure of the cylinder shell is detected. An analysis unit determines a dent depth from a data memory at which a dent force at a complete failure of the cylinder shell is at a maximum compared to dent forces of other dent depths.

11 Claims, 3 Drawing Sheets

(58) Field of Classification Search
CPC .............. G01N 3/20; G05B 19/4067; G05B 2219/50097; G05B 2219/50353; G05B 2219/50098
See application file for complete search history.

(56) References Cited

U.S. PATENT DOCUMENTS

2016/0187230 A1* 6/2016 Wang .................. B64C 1/068
702/43
2016/0224007 A1 8/2016 Zeniya et al.

* cited by examiner

DEVICE FOR DETERMINING THE LOAD-BEARING CAPACITY OF A CYLINDRICAL SHELL INCLUDING AN AXIAL WORKING FORCE TO THE CYLINDRICAL SHELL AND DETECTING FAILURE OF THE CYLINDRICAL SHELL

FIELD OF THE INVENTION

The invention concerns a device for determining the load-bearing capacity of cylindrical shells of a composite fiber material that is at risk of buckling.

BACKGROUND

Thin-walled structures, such as for example circularly cylindrical shells, tend to form a buckling pattern under axial pressure load, so that large deformations occur perpendicular to the direction of the axial pressure load. Such a buckling pattern can for example be formed circumferentially, which is also understood to mean a global buckling. Said global buckling patterns often arise suddenly and without prior notice, wherein the axial load-bearing capacity of the structure is significantly reduced by said deformation (buckling).

The cause of said deformation, and hence the accompanying strong reduction of the possible axial load-bearing capacity, can for example be manufacturing-related deviations in the geometry (geometric "mid-surface" imperfections MSI) or deviations from the ideal homogenous loading (geometric "boundary condition" imperfections BCD. In this case, said deviations from the geometry or the ideal homogenous loading can significantly reduce the maximum possible load-bearing capacity of a cylindrical shell, so that this is very important in the planning and development of thin-walled structures, in particular in air travel and space travel.

In the 1950s and 1960s, many buckling tests on thin-walled cylindrical shells of isotropic materials and substances, such as for example steel or aluminum, were carried out. In order to derive the design load $N_{NASA}$, the non-linear buckling load $N_{n-lin}$ of the perfect shell, i.e. without imperfections, is required, wherein the non-linear buckling load is reduced by a reduction factor $p_{NASA}$ as a function of the slenderness R/t (quotient of radius R and wall thickness t), in order to take into account the imperfections of the cylindrical shell. The design load $N_{NASA}$ can be calculated using the following equation:

$$N_{NASA} = N_{n-lin}^{per} \cdot p_{NASA}.$$

The reduction factor is in this case the quotient of the experimental and theoretical linear buckling loads of an ideal perfect shell and decreases with increasing slenderness.

SUMMARY

The known reduction factors are very conservative in relation to cylindrical shells of a composite fiber material, for example of a carbon composite fiber material. The reason for this is that a series of test results have been found in the test results based on reduction factors that do not correspond to the current state of the art in relation to the quality of the generation of the test using the cylindrical shells, the performance of the test and the analysis of the test. In addition, the layered structure of the composite fiber shells is only taken into account to a very small extent. In this case, in particular the sensitivity to imperfections of the cylindrical shells of a composite fiber material, which depends on the layered structure of the composite fiber cylindrical shells, is not taken into account.

It is therefore the object of the present invention to specify an improved device, with which the load-bearing capacity of cylindrical shells that are at risk of buckling of a composite fiber material can be determined, in order for example to derive improved reduction factors for analytical calculation of the design load, which enables an improved approximation to the actual load-bearing capacity.

According to the invention, a device for determining the load-bearing capacity of cylindrical shells of a composite fiber material that are at risk of buckling is provided, wherein the device comprises a load distribution head that is designed for applying an axially acting force to a cylindrical shell introduced into the device. In this case a cylindrical shell means a rotationally symmetrical body that comprises a uniform radius or a radius that varies along the axis of rotation. A cylindrical shell can thus comprise an axially constant cross-section or an axially varying cross-section if the cylindrical shell is for example a conical cylindrical shell. The cylindrical shell comprises in this case an upper and a lower end, which are the axial limits of the cylindrical shell. As a rule, such cylindrical shells are open at the upper and lower ends thereof. For the purposes of the present invention, in this case the upper end of the cylindrical shell means the side or the end of the cylindrical shell at which the load distribution head contacts the cylindrical shell for applying an axially acting force, whereas the lower end of the cylindrical shell is the end at which the cylindrical shell is fixed, so that the axially acting force can for example be dissipated through the cylindrical shell to a base. The upper end of the cylindrical shell can also be referred to as the first end, whereas the lower end is defined as the second end.

Furthermore, the device comprises a dent actuator that is designed to produce a defined single dent in the surface of the cylindrical shell. Here the defined single dent is introduced by the dent actuator into the surface of the cylindrical shell so that the single dent is produced in a predetermined dent direction with a predetermined dent depth. Using the dent actuator, which can for example be a linear actuator with a tip that applies a force radially from out to in to the surface of the cylindrical shell in order to produce the single dent in a defined dent direction and with a defined dent depth, a defined imperfection can be introduced into the cylindrical shell in order to be able to determine a corresponding load behavior when producing or applying the axially acting force by means of the load distribution head.

Furthermore, the device comprises a fixed support that is disposed opposite to the actuator direction in order to fix the dent depth in the dent direction. The single dent is located between the dent actuator and the fixed support, i.e. it is thus a part of the cylindrical shell, wherein the dent depth is fixed by the fixed support in the dent direction in the case of an axial loading of the cylindrical shell, and thus the dent depth does not increase and no longer changes in the event of an axially acting force through the load distribution head.

Furthermore, a dent force sensor is provided, which for example is disposed on the dent actuator or on the fixed support and which is designed for determining a dent force of a single dent that is fixed in the dent direction if a steadily increasing axially acting force is applied to the cylindrical shell by the load distribution head. This enables the force in the dent direction to be measured that is exerted on the single dent in the case of the steadily increasing axially acting force, whereby, as will be shown below, the corresponding load behavior and therefrom the load-bearing capacity can be derived.

Furthermore, a control unit is provided that is designed for actuating the load distribution head to apply a steadily rising, axially acting force to the cylindrical shell. In this case, the control unit is designed so that the load distribution head is actuated such that the axially acting force that is applied to the cylindrical shell is steadily increased until a complete failure of the cylindrical shell is detected as a load step by an axial force sensor. Said axial force sensor can for example be disposed in the load distribution head or the opposing base and continuously measures the axially acting force that is applied by the load distribution head to the cylindrical shell. If the cylindrical shell now gives way because of the axially acting force and there is complete failure of the cylindrical shell, then the failure can be detected by an abrupt load step in the measured axially acting force, because as a rule the already mentioned global buckling arises as a result of a complete failure of the cylindrical shell and the cylindrical shell has a number of imperfections on its periphery.

Finally, a digital data memory is provided that is arranged for storing the respective current dent force for a complete failure of the cylindrical shell and the axially acting force that is applied to the cylindrical shell with the current dent force for the respectively set dent depth. Thus, for each dent depth that has been set and suitably fixed, an axially acting load profile can be stored together with the dent force correlated therewith, wherein in particular the value of the dent force and the axially acting force at which the complete failure of the shell is detected are of interest. In doing so, for different dent depths there is a correlation pattern between the dent force and the axially acting force, from which finally the maximum load-bearing capacity of such a cylinder shell that is at risk of buckling can be derived. Using the present invention, it is thus possible for the first time to investigate and determine the load-bearing capacity of cylindrical shells of a composite fiber material with predetermined and defined imperfections without having to take into account great uncertainties and unknowns for this purpose.

Advantageously, the dent actuator is arranged for producing a defined single dent in a radially inward dent direction in the cylindrical shell, wherein the fixed support is arranged in an internal space of the cylindrical shell for fixing the radially inwardly directed single dent. However, it is also conceivable that the dent actuator is disposed in an internal space of the cylindrical shell and is designed for producing a defined single dent in the cylindrical shell in a radially outward dent direction, wherein the fixed support is then arranged in an outer region of the cylindrical shell to fix the outwardly directed single dent.

Advantageously, the dent force sensor for determining the dent force is disposed within a load path of the fixed support or within a load path of the dent actuator in order to be able to determine the dent force while the axially acting force is acting.

Advantageously, the dent force sensor can for example be a force measurement cell that is disposed in the linear-acting dent actuator, preferably on the tip of the dent actuator. However, it is also conceivable that the dent force sensor is a strain gauge that is disposed in the region of the fixed support and can measure the dent force there while the axially acting force is acting.

In a further advantageous embodiment, the dent actuator works together with a dent depth controller to set a predetermined dent depth, so that the dent actuator induces a single dent having a predetermined and defined dent depth. Here it is for example conceivable that by means of a variable stop the dent actuator can work together with the dent depth controller so that a maximum adjustable dent depth of the single dent that is to be produced can be defined.

In a further advantageous embodiment, the device comprises an analysis unit that is arranged for determining the dent depth from the data memory for which the dent force is at a maximum in the event of complete failure of the cylindrical shells compared to the dent forces of the other dent depths, wherein the axially acting force on the cylindrical shell for which a complete failure of the cylindrical shell has been detected for said determined dent depth is output by the analysis unit as the maximum load-bearing capacity of the cylinder shell that is at risk of buckling. It has thus been recognized that the axially acting force at which the dent force for a predetermined dent depth is at a maximum above the dent forces for the other dent depths for a total failure of the cylinder structure can be seen as the permitted load-bearing capacity of the cylinder structure that is at risk of buckling.

This enables the load-bearing capacity for so-called manufacturing-related deviations of the geometry (geometric "mid-surface" imperfections MSI) to be determined, so that an important component of the determination of the permitted load-bearing capacity of cylindrical shells can be specified therefrom.

In a further advantageous embodiment, the device comprises a bending device that is arranged for producing a bending stress in the cylindrical shell by rotating the cylindrical shell's upper cross-sectional plane, which is formed by the upper end of the cylindrical shell, relative to the cylindrical shell's lower cross-sectional plane, which is formed by the lower end of the cylindrical shell, by a predetermined bending angle. This enables the cylindrical shell to be variously loaded over the periphery thereof, whereby in particular deviations from the ideal homogenous loading (geometric "boundary condition" imperfections BCI) can be tested.

In this regard, it is advantageously provided that the bending device has one or more adapter plates comprising an inclination corresponding to a predetermined bending angle and designed to be introduced into the device between the cylindrical shell's upper cross-sectional plane and the load distribution head or between the cylindrical shell's lower cross-sectional plane and a supporting base of the device in order to adjust the bending angle. Here the adapter plate is first inserted at the predetermined position and then the load distribution head is lowered and loaded, so that a force acts axially on the adapter plate and thereby on the cylindrical shell. Because of the inclination of the adapter plate, the cylindrical shell is more strongly loaded on one side than on the opposite side, so that bending of the cylindrical shell is set up, whereby a bending stress is introduced into the cylindrical shell.

Alternatively or additionally, it is also conceivable that the load distribution head is designed for rotating the upper cylindrical shell through the cross-sectional plane by a predetermined bending angle, so that the use of adapter plates can be omitted accordingly. The load distribution head is designed so that besides a purely axially acting force, a rotational moment or a tilting moment can be produced, whereby the cylindrical shell is loaded on one side and a bending stress is produced in the cylindrical shell.

Hereby it is quite particularly advantageous if rotating the cylindrical shell's upper cross-sectional plane, be it only by means of the load distribution head or by means of an adapter plate, is designed to rotate the cylindrical shell's upper cross-sectional plane relative to the cylindrical shell's lower cross-sectional plane in the direction of the single dent that has been produced. This means that the tilting or the inclination of the cylindrical shell's upper cross-sectional plane aligns with the single dent that is disposed under the cylindrical shell's upper cross-sectional plane, so that the distance between the lower end of the cylindrical shell in the upper end of the cylindrical shell is at its smallest in the region of the single dent.

Advantageously, the digital data memory is arranged in this case for storing the current buckling force of the axially acting force applied to the rotated cylindrical shell with the current dent force for the respective set dent depth in combination with the predetermined bending angle in order to be able to determine the maximal permitted load-bearing capacity or design load.

Therefore it is advantageous if an analysis unit is provided that is arranged to determine a minimum load path of the axially acting force at which a complete failure of the cylindrical shell has been detected over various bending angles from a number of axially acting forces at which a complete failure of the cylindrical shell has been detected for predetermined bending angles and dent depths, and to determine the load-bearing capacity of the cylinder shell that is at risk of buckling depending on the minimum load paths.

DESCRIPTION OF THE DRAWINGS

The invention is described using the accompanying figures by way of example.

In the figures.

DETAILED DESCRIPTION

Figure 1:
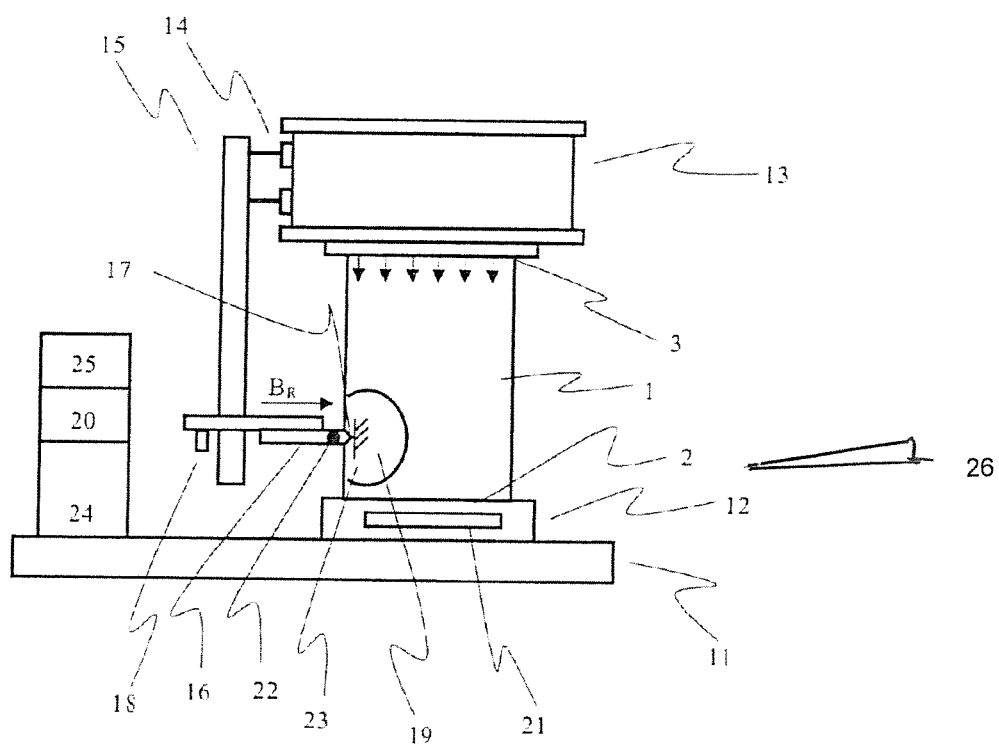
FIG. 1—shows a schematic representation of the device according to the invention for determining the load-bearing capacity.

FIG. 1 shows schematically the device 10 according to the invention, which has a tool bench 11 and a stop or base 12 connected thereto. A cylindrical shell 1 that rests with the lower end 2 thereof on the base 12 of the workbench 11 is placed on the base. On the upper end 3 opposite the lower end 2, the cylindrical shell 1 is contacted by a load distribution head 13, wherein the load distribution head 13 is designed for applying an axially acting force towards the cylindrical shell 1 (illustrated by the arrows at the upper end 3 of the cylindrical shell 1).

A mounting arm 15, on which a dent actuator 16 is disposed axially displaceably relative to the cylindrical shell 1, is removably disposed on the load distribution head 13 by means of a magnet arrangement 14. The dent actuator 16 is in this case designed for inducing a single dent 17 in the cylindrical shell 1 or the surface of the cylindrical shell in the direction $B_R$, which is directed radially towards the interior of the cylindrical shell 1. The dent depth of the single dent 17 can be adjusted in this case using a dent depth controller 18.

Moreover, a fixed support 19 is provided within the cylindrical shell 1, which fixes the single dent 17 in the dent direction $B_R$ in the event of an axially acting force applied by the load distribution head 13, so that the dent depth essentially remains constant even while the axially acting force and the steadily rising axially acting force are acting.

Furthermore, the device 10 comprises a control unit 20 with which the load distribution head 13 as well as the dent actuator 16 can be suitably actuated.

Furthermore, in the exemplary embodiment of FIG. 1 a force sensor 21 is provided in the base 12, which is designed for measuring the axially acting force on the cylindrical shell 1 that is applied by the load distribution head 13.

Furthermore, the dent actuator 16 comprises a force measurement cell 22, with which the dent force in the dent direction $B_R$ can be measured while the axially acting force applied by the load distribution head 13 is acting. This enables conclusions to be drawn regarding the force conditions within the single dent, in particular the force conditions in the dent direction $B_R$, in order for example to be able to make a statement about the geometric imperfections.

Alternatively or additionally, it is also conceivable that a strain gauge 23 is disposed on the fixed support 19 in order to be able to determine the bending direction caused by an adapter plate 26 having a predetermined bending angle which is inserted between the cylindrical shell 1 and the base 12 or between the cylindrical shell 1 and load distribution head 13 while the axially acting force is acting.

The control unit 20 can furthermore comprise a data memory 24 in order to be able to suitably store the data and data correlations obtained during the individual measurements that are carried out using the device 10. Using an analysis unit 25, corresponding statements about the permitted load-bearing capacity of cylindrical shells that are at risk of buckling can then be derived.

Figure 2:
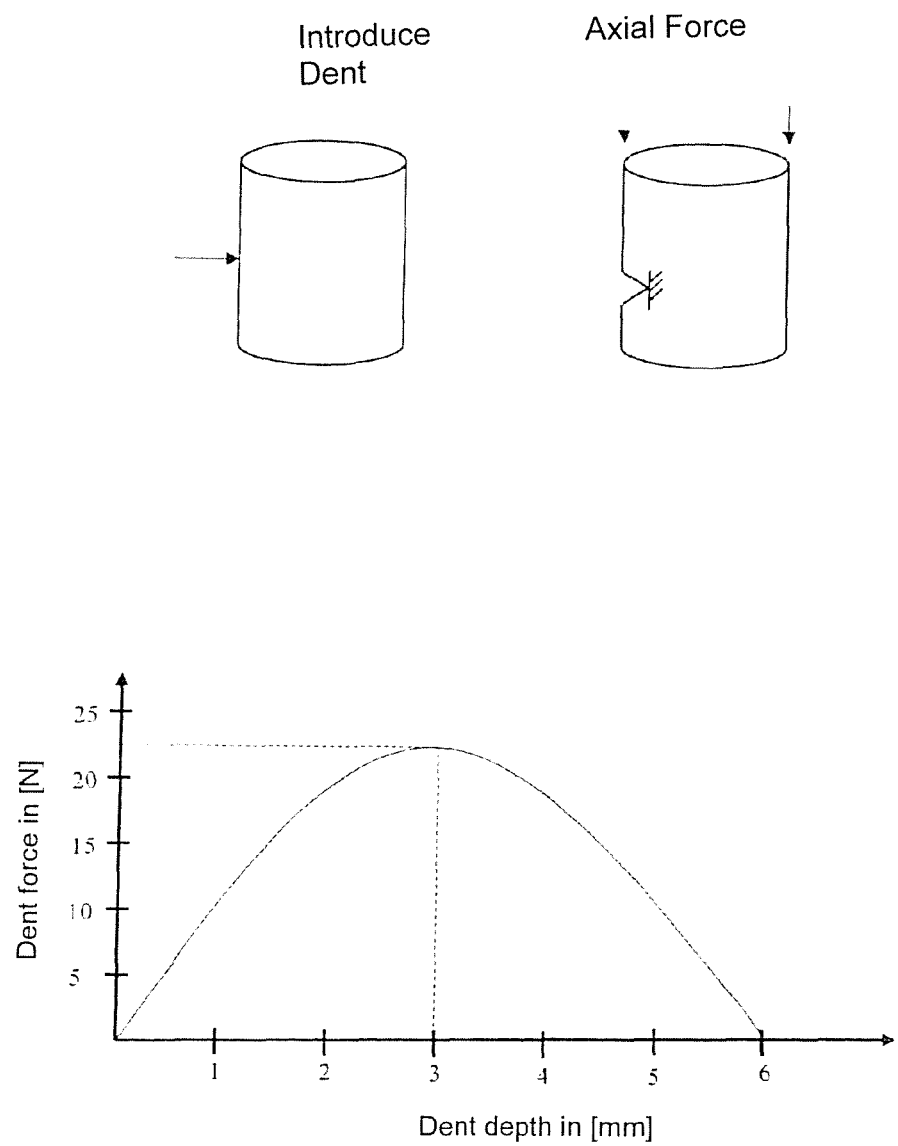
FIG. 2—shows a diagram for determining geometric imperfections.
Figure 3:
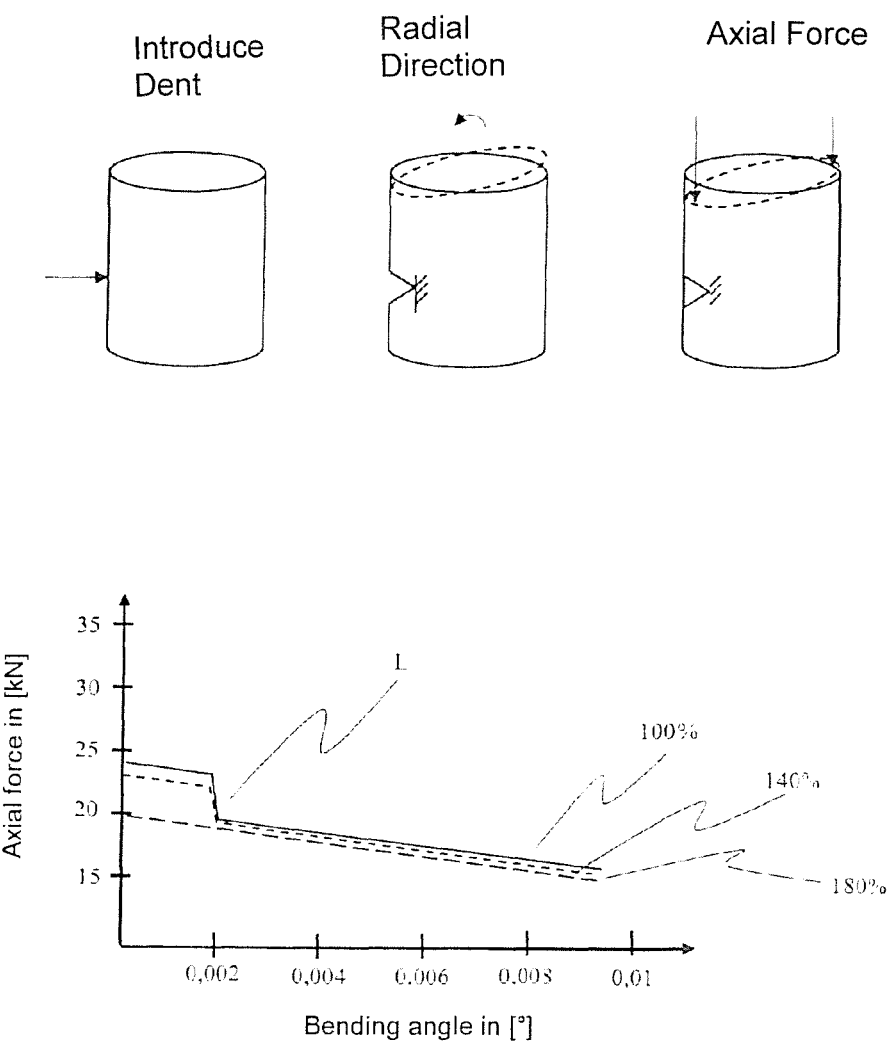
FIG. 3—shows a diagram for estimating "boundary condition" imperfections.

FIGS. 2 and 3 show suitable diagrams for this, with which suitable boundary conditions for the load-bearing capacity can be calculated. In doing so, various series of measurements are carried out using the device 10, wherein the corresponding load-bearing capacity data can be determined very accurately from the data that are obtained as a result. In step 1 a single dent is introduced in the predetermined dent direction and with a defined dent depth and is fixed with a fixed support. In step 2, an axially acting force is then applied to the cylindrical shell, wherein during the step the dent force acting in the radial direction in the single dent that is induced is detected while the steadily rising axially acting force is acting on the cylindrical shell. This results in a continuous data pair between the axially acting force on the one hand and the dent force on the other hand, wherein using a load step the axially acting force at the time of a complete failure of the cylindrical shell can then be identified. The axially acting force on the cylindrical shell that is set at the point in time of the complete failure and the dent force acting at said point in time are of particular significance here.

During this, step 2 is repeated for various dent depths or impression depths of the single dent, so that a respective dent force can then be determined for various dent depths, which has been measured at the point in time of the complete failure of the cylindrical shell. This is illustrated in FIG. 2. It can be seen that the dent force initially increases for various impression depths or dent depths, while it has reached the maximum thereof at a dent depth of 3 mm. During this, the dent force plotted on the Y-axis is the dent force that was measured at the point in time of the complete failure of the cylinder structure. For larger dent depths, it is determined here that the dent force that was measured at the point in time of the complete failure of the cylinder structure decreases again, so that a maximum dent force can be measured at a dent depth of 3 mm.

The diagram shown in FIG. 2 is to be considered exemplary here and should only be used as an explanation of the measurement methodology. Depending on the cylindrical shell and the properties thereof, i.e. the materials used, the radius as well as the wall thickness, quite different diagrams result for this purpose.

The maximum of the dent force derived from said diagram is thus reached at a dent depth of 3 mm, wherein a stop point for the so-called geometric imperfections is now formed based on the axially acting force at the point in time of the complete failure of the cylinder structure, which has been measured for said dent depth of 3 mm for a corresponding dent force. Here it was recognized that said axially acting force, which was measured for the complete failure of the cylinder structure at the dent depth that correlates with the maximum dent force at the point in time of the complete failure (according to FIG. 2 a dent depth of 3 mm), gives a very good approximation to the possible load-bearing capacity the cylinder structure, and indeed in conjunction with the so-called geometric "mid-surface" imperfections (MSI).

In step 3, the deviation from the ideal homogenous loading, the so-called geometric "boundary condition" imperfections (BCI), is now sought based on the results of step 2. For this purpose, the dent depth determined from step 2 (3 mm in FIG. 2) is induced in the form of a single dent using the device according to the invention, wherein using the device a bending stress is then introduced into the cylindrical shell towards the induced single dent. This can for example take place owing to the fact that the load distribution head 13 of the device 10 is designed to be rotatable, tiltable or pivotable, whereby the upper end 3 can be rotated or tilted relative to the lower end 2 of the cylindrical shell (not in connection with a magnetic arrangement of the dent actuator on the load distribution head). If a suitable bending angle is set, then the cylindrical shell is axially loaded again using the load distribution head 13, wherein the single dent is fixed at the value determined in step 2 regarding the dent depth thereof. In this case the cylindrical shell with the set bending angle is axially loaded until a complete failure of the cylinder structure can be detected again. During this, the axial force applied at the point in time of the complete failure of the cylinder structure is stored in a data memory together with the set bending angle and possibly the set dent depth.

Said series of measurements is now repeated for various bending angles, wherein the bending angle is steadily increased here. In this case, it can be seen that for a defined bending angle a load step relating to the axially acting force relative to the preceding measurement with the small bending angle can suddenly be detected at the point in time of the complete failure, as marked in FIG. 3 by L. The subsequent measurements then show an essentially homogenous load path, which is reduced by the load step 11 to the preceding measurements before the load step. It has been found that the axially acting force at which the entire structure fails and that has been measured for the bending angles that lie after the load step represents a homogenous equilibrium path that indicates the maximum load-bearing capacity of said cylinder structure.

This can be verified, for example, by increasing the dent depth by 40% or 80%. It can be seen here that when the dent depth is increased by 40% for an almost identical bending angle, a corresponding load step can be detected. Furthermore, for an 80% increase in the impression depth or dent depth it can be determined that it moves essentially on the homogenous load path almost without a load step, so that a very accurate estimate of the possible load-bearing capacity of the cylinder structure can be output here.

In summary, it can therefore be said that with the new test method a specific instability point for geometric "mid-surface" imperfections of shell structures can be determined, wherein the structure can then be forced onto a particularly stable equilibrium path with said instability point, wherein the load-bearing capacity on said equilibrium path then provides a limit value for the real load-bearing capacity. Using the present device, a corresponding real measurement of cylindrical shells is necessary in order to carry out such a test method.

REFERENCE CHARACTERS 10 device
11 tool bench
12 base
13 load distribution head
14 magnet arrangement
15 mounting arm
16 dent actuator
17 single dent
18 dent depth controller
19 fixed support
20 control unit
21 force sensor
22 force measurement cell
23 strain gauge
24 data memory
25 analysis unit
$B_R$ dent direction

The invention claimed is:

1. A device for determining the load-bearing capacity of cylinder shells that are at risk of buckling of a composite fiber material, comprising:
   a load distribution head which applies an axially acting force to a cylinder shell introduced into the device;
   a dent actuator which produces a single dent in a surface of the cylinder shell in a predetermined dent direction with a predetermined dent depth;
   a fixed support which fixes the dent depth of the single dent produced by the dent actuator in the predetermined dent direction;
   a dent force sensor which determines a dent force in the predetermined dent direction of the single dent that is fixed in the predetermined dent direction when a steadily increasing, axially acting force is applied to the cylinder shell by the load distribution head;
   a control unit which actuates the load distribution head for applying a steadily increasing, axially acting force to the cylinder shell until a complete failure of the cylinder shell is detected as a load step by an axial force sensor;
   a digital data memory which stores a current dent force in an event of a complete failure of the cylinder shell and the applied axially acting force on the cylinder shell at the current dent force for the predetermined dent depth; and
   an analysis unit which determines a dent depth from the data memory at which a dent force at a complete failure of the cylinder shell is at a maximum compared to dent forces of other dent depths, wherein the axially acting force on the cylinder shell at which the complete failure of the cylinder shell has been detected for the determined dent depth is output by the analysis unit as a load-bearing capacity of the cylinder shell that is at risk of buckling.

2. The device as claimed in claim 1, wherein the dent actuator produces the single dent radially inwards into the cylinder shell, and wherein the fixed support is located in an internal space of the cylinder shell.

3. The device as claimed in claim 1 wherein the dent force sensor is disposed in a load path of the fixed support or in a load path of the dent actuator.

4. The device as claimed in claim 1 wherein the dent force sensor is a force measurement cell or a strain gauge.

5. The device as claimed in claim 1 wherein the dent actuator works in conjunction with a dent depth controller for setting the predetermined dent depth.

6. The device as claimed in claim 1 further comprising a bending device which produces a bending stress in the cylinder shell by rotating an upper cross-sectional plane of the cylinder shell relative to a lower cross-sectional plane of the cylinder shell by a predetermined bending angle.

7. The device as claimed in claim 6, wherein the bending device has one or more adapter plates for setting a bending angle, the one or more adapter plates having an inclination corresponding to the predetermined bending angle for introduction into the device between the cylinder shell's upper cross-sectional plane and the load distribution head and/or between the cylinder shell's lower cross-sectional plane and a supporting base of the device.

8. The device as claimed in claim 6 wherein the bending device is designed for turning the load distribution head for rotating the cylinder shell's upper cross-sectional plane by the predetermined bending angle.

9. The device as claimed in claim 6 wherein the bending device is designed for turning the cylinder shell's upper cross-sectional plane relative to the cylinder shell's lower cross-sectional plane by the predetermined bending angle in the direction of the single dent that is produced.

10. The device as claimed in claim 6 wherein the digital data memory stores the current dent force and the axially acting force applied to the cylinder shell with the current dent force for the respective set dent depth in conjunction with the predetermined bending angle.

11. The device as claimed in claim 6 wherein the analysis unit is arranged to determine a minimum load path of the axially acting force at which a complete failure of the cylinder shell has been detected using various bending angles and from a number of axially acting forces at which a complete failure of the cylinder shell has been detected for predetermined bending angles and dent depths, and to determine the load-bearing capacity of the cylinder shell that is at risk of buckling depending on the minimal load path.

* * * * *